United States Patent [19]

Gordon

[11] 4,289,890

[45] Sep. 15, 1981

[54] SYNTHESIS OF CHLOROMETHYLDISILANES

[76] Inventor: Roy G. Gordon, 22 Highland St., Cambridge, Mass. 02138

[21] Appl. No.: 92,205

[22] Filed: Nov. 7, 1979

Related U.S. Application Data

[63] Continuation-in-part of Ser. No. 11,079, Feb. 12, 1979.

[51] Int. Cl.$^3$ .......................... C07F 7/08; C07F 7/16; C07F 7/14; C07F 7/12
[52] U.S. Cl. ................................................. 556/430
[58] Field of Search ................. 260/448.2 E; 556/430

[56] References Cited

U.S. PATENT DOCUMENTS

| | | | |
|---|---|---|---|
| 2,598,435 | 5/1952 | Mohler et al. | 260/448.2 E |
| 4,059,607 | 11/1977 | Reedy et al. | 260/448.2 E |
| 4,059,608 | 11/1977 | Calas et al. | 260/448.2 E |

*Primary Examiner*—Paul F. Shaver
*Attorney, Agent, or Firm*—Robert A. Cesari; John F. McKenna; Andrew F. Kehoe

[57] ABSTRACT

1,2 Dichloro-1,1,2,2-tetramethyldisilane is synthesized in high yield and good purity starting from a crude mixture of chloromethyldisilanes formed as by-products in the manufacture of silicones. The new method uses less than half as much Grignard reagent as previous methods required. The synthesis can also be used to produce other haloalkyldisilanes such as chloropentamethyldisilane or 1,1,2 trichloro-1,2,2-trimethyldisilane.

22 Claims, No Drawings

SYNTHESIS OF CHLOROMETHYLDISILANES

RELATED APPLICATION

This invention is a continuation-in-part of Applicant's co-pending U.S. patent application Ser. No. 11,079 filed FEB. 12, 1979.

BACKGROUND

Alkylhalodisilanes are well known in the art. For example, methylchlorodisilanes have the general formula $Me_{6-x}Si_2Cl_x$, where Me stands for the methyl group $CH_3$, and $x = 1, 2, 3, 4$ or $5$. These compounds are chemical intermediates useful in forming a wide variety of compounds, particularly those compounds containing silicon-silicon bonds. One use of alkylhalodisilanes is that wherein the reduced disilane is oxidized in a system in which tetramethyl tin is also oxidized, thereby permitting codeposition of a mixed oxide coating on glass.

Six previously developed methods for preparing chloromethyldisilanes begin with a mixture called the "disilane fraction," which is a by-product from the manufacture of methylchlorosilane monomers. This disilane fraction, typically boiling between 150° C. and 160° C., consists mainly of 1,1,2,2 tetrachlorodimethyldisilane and 1,1,2 trichlorotrimethyldisilane. Thus the starting material already contains the Si-Si bond of the desired product, and the synthesis is designed to replace some of the methyl groups with the desired number of chlorine atoms.

A Grignard reaction, e.g., one utilizing methyl magnesium chloride in ether, is a common way to replace chlorines with methyl groups. However, the Grignard reaction applied to the disilane fraction cannot be stopped conveniently at a partial replacement of chlorine by methyl. Thus, the fully methylated product hexamethyldisilane ($Me_3SiSiMe_3$) results. This is shown by Kumada and Yamaguchi (1954). A successful partial Grignard reaction was obtained by Kumada et al (1956), by first converting the disilane fraction to its ethoxy derivative with ethanol/ammonia. After the partial Grignard reaction, the product is reconverted to the chloride with acetyl chloride. The overall yield of 1,2 dichlorotetramethyldisilane was only about 30%.

Another approach to the synthesis of these disilanes is to form the hexamethyldisilane by complete Grignard treatment of the disilane fraction itself, and then to partially chlorinate the resulting hexamethyldisilane. A successful synthesis by this approach was developed by Kumada et al. (1956), using sulfuric acid followed by ammonium chloride, giving a yield of 55% after a total reaction period of 2 days. Later workers discovered better chlorinating agents which increased the yield and decreased the reaction time: Sakurai et al. (1966, 1967) found that dry hydrogen chloride in the presence of $AlCl_3$ catalyst rapidly chlorinated hexamethyldisilane to 1,2 dichlorotetramethyldisilane with an improved yield of 81%. They also found that by using large amounts of aluminum chloride, acetyl chloride could also be used to chlorinate hexamethyldisilane, with 87% yield of 1,2 dichlorotetramethyldisilane. However, a disadvantage of using acetyl chloride is that the subsequent separation of the large amounts of aluminum chloride from the product is difficult. Probably the most satisfactory chlorinating agent previously found for hexamethyldisilane is trimethylchlorosilane, $Me_3SiCl$, which Ishikawa et al. (1970) found to give a 93% yield of 1,2 dichlorotetramethyldisilane.

A disadvantage of the methods based on chlorination of hexamethyldisilane is that the major part of the Grignard reagent is wasted, in the sense that most of its methyl groups end up in by-products, rather than in the 1,2 dichlorotetramethyldisilane. Typically, one adds about 3.5 methyl groups per molecule of disilane to form the hexamethyldisilane and then removes 2 of them during the subsequent chlorination. A recent synthesis by Matsumoto et al. (1977) avoids this use of large amounts of Grignard reagent by partial methylation of the disilane fraction using trimethylchlorosilane. The yield is, only about 43% even after 2 successive methylations.

Most of these known synthetic methods have also been adapted to product 1,1,2 trichlorotrimethyldisilane and chloropentamethyldisilane, by changing reactant proportions and/or reaction temperatures, but the same basic disadvantages remain in such analogous procedures.

The following published references are pertinent to the above discussion:

(1) Kumada and Yamaguchi, J. Chem. Soc. Japan, Ind. Chem. Sect. (1954), vol. 57, pp. 175–177.
(2) Kumada et al., J. Org. Chem. (1956), vol. 21, pp. 1264–1268.
(3) Sakurai et al. Tetrahedron Letters (1966), vol. 45, pp. 5493–5497.
(4) Sakurai et al., J. Organometallic Chem. (1967), vol. 7, pp. P15–P16.
(5) Ishikawa et al., J. Organometallic Chem. (1970), vol. 23, pp. 63–69.
(6) Matusomoto et al., J. Organometallic Chem. (1977), vol. 142, pp. 149–153.
(7) Japanese Patent Publication 70/12726 to Kumada, Ishikawa

SUMMARY OF THE INVENTION

Consequently, it is a principal object of the present invention to provide an improved process for making halogenated polyalkyldisilane. It is a particular object of the invention to provide an improved process for making 1,2 dichlorotetramethyldisilane; 1,1,2 trichlorotrimethyldisilane and chloropentamethyl disilane.

A more specific object of the invention is to provide processes which combine the attributes of economy, high yields, dependability and a processing cycle which is less time-consuming. Other objects of the invention will be obvious to those skilled in the art on their reading of this disclosure.

DESCRIPTION OF NEW SYNTHESIS OF 1,2 DICHLOROTETRAMETHYLDISILANE, 1,1,2 TRICHLOROTRIMETHYLDISILANE, OR CHLOROPENTAMETHYLDISILANE

It has now been discovered that hexamethyldisilane can be readily chlorinated using the disilane fraction to give high yields, often over 75 to 80%, of 1,2 dichlorotetramethyldisilane. The main reactions may be written $$Me_6Si_2 + Me_2Si_2Cl_4 \rightarrow 2Me_4Si_2Cl_2 \qquad (I)$$

$$Me_6Si_2 + 2Me_3Si_2Cl_3 \rightarrow 3Me_4Si_2Cl_2 \qquad (II)$$

Thus the desired product is obtained directly in fairly pure form with neither any major amount of by-product nor any solvent which need be separated. Another major advantage of this synthesis is that all of the methyl groups added in the Grignard reaction forming hexamethyldisilane are retained in the product. In the prior chlorination methods, more than half of the added methyl groups are wasted by appearing in by-products. Thus less than half as much Grignard reagent is required in the new process as was required in the previous methods.

The complete new synthesis begins with the disilane fraction. One portion of the disilane fraction is completely methylated to hexamethyldisilane using standard Grignard methods, or other such convenient methylating procedures. The hexamethyldisilane is then mixed with a second portion of disilane fraction to form a homogeneous liquid solution. This solution is heated in the presence of a suitable catalyst such as $AlCl_3$ or $NaAlCl_4$, to form the desired product according to the reactions I and II above. By adjusting the sizes of the two portions, the major product can be made to be either 1,1,2 trichlorotrimethyldisilane, or 1,2 dichlorotetramethyldisilane, or chloropentamethyldisilane.

A typical disilane fraction consists of about equal amounts of 1,1,2,2 tetrachlorodimethylsilane ($Me_2Si_2Cl_4$) and 1,1,2 trichlorotrimethyldisilane ($Me_3Si_2Cl_3$), corresponding to an empirical formula $Me_{2.5}Si_2Cl_{3.5}$. Thus the stoichiometry of the synthesis of 1,2 dichlorotetramethyldisilane ($Me_4Si_2Cl_2$) may be described by $$3Me_{2.5}Si_2Cl_{3.5} + 10.5\ MeMgCl \rightarrow 3Me_6Si_2 + 10.5\ MgCl_2 \quad (III)$$

$$4Me_{2.5}Si_2Cl_{3.5} + 3Me_6Si_2 \rightarrow 7Me_4Si_2Cl_2 \quad (IV)$$

In other words, for this case seven (7) parts of the disilane fraction are divided into three (3) parts which are methylated by the Grignard reaction, and the resulting hexamethyldisilane combined with the other four (4) parts of the original disilane fraction, to produce mainly $Me_4Si_2Cl_2$.

To produce mainly 1,1,2 trichlorotrimethyldisilane from a disilane fraction of the above typical composition, one methylates one mole of a first portion of the disilane fraction and then reacts the resulting hexamethyldisilane with six moles of the second portion of disilane fraction. If the desired product is chloropentamethyldisilane, one methylates five moles of the initial portion of disilane fraction and reacts this with two moles of the second portion of disilane fraction.

Because the composition of the disilane fraction varies somewhat from batch to batch, depending on the details of the manufacturing conditions, it is best to base the proportions used on an actual batch analysis.

However, one important advantage of this process is that an error in the proportions actually used can be corrected even after an "erroneous" synthesis is complete. Suppose a "finished" product is analyzed to contain 60% of the desired product, $Me_4Si_2Cl_2$ and 40% of an unwanted impurity, $Me_5Si_2Cl$. By adding an additional 20% of the original disilane fraction $Me_{2.5}Si_2Cl_{3.5}$ and reheating in the presence of the catalyst, one may convert the batch to better than 80% purity of the desired product.

The reaction between hexamethyldisilane and the disilane fraction is conveniently carried out by heating the mixture under reflux at atmospheric pressure. The reflux system should be free of moisture. In the absence of a catalyst, the reaction is undesirably slow. For example, refluxing of an available commercial by-product disilane fraction for three days in the absence of a catalyst resulted in no measurable product. Some substances which catalyze the reaction include aluminum chloride $AlCl_3$, sodium chloroaluminate $NaAlCl_4$, boron trichloride $BCl_3$, gallium trichloride $GaCl_3$, zirconium tetrachloride $ZrCl_4$ and tin tetrachloride $SnCl_4$. Aluminum chloride is often a preferred catalyst, since it is quite active even at a concentration of only one (1) percent by weight, and it is inexpensive and readily available. Aluminum chloride seems to vary somewhat in catalytic activity as obtained from different commercial sources. Iron chloride impurities in the aluminum chloride seem to be deleterious, but other presently unknown factors may influence the catalytic activity. It is best, therefore, to monitor the reaction by periodic sampling to determine when the product has reached a maximum purity or yield, as desired. Prolonged refluxing in the presence of aluminum chloride should be avoided, since this can lead to deleterious polymerization reactions, to cleavage reactions, or to both kinds of undesirable reactions.

The one disadvantage of aluminum chloride as a catalyst is that it is difficult to remove it entirely from the product. Distillation of 1,2 dichlorotetramethyldisilane (B.P. 148° C.) is not completely effective in removing aluminum chloride (B.P. 178° C.). For some purposes, the presence of aluminum chloride in the product may not be disadvantageous. However, if it is desired to have a product relatively free of aluminum chloride, then sodium chloroaluminate, $NaAlCl_4$, is a better choice of catalyst. $NaAlCl_4$ is practically insoluble in the methylchlorodisilanes. The catalyst $NaAlCl_4$ is conveniently supported on pellets of silica, alumina, etc., having a high surface area.

I have found that the reaction can be speeded up still more by the addition of a few percent of reduced disilane compounds of the type $Me_{6-x}Si_2H_x$, where $x = 1, 2, 3$ or 4, to the catalysts disclosed above. These reduced disilanes alone do not function as effective catalysts. Therefore they can be said to act as co-catalysts, which enhance the activity of the primary catalysts such as $AlCl_3$, $NaAlCl_4$, or the like.

In this application, the term "disilane fraction" is defined as those disilane compositions known to be available as commercial by-products of the manufacture of the methylchlorosilane monomers used in preparation of silicone polymers and which are exemplified by that disilane fraction which typically boils between 148° C. and 160° C. and consists primarily of 1,1,2,2 tetrachloromethyldisilane and 1,1,2 trichlorotrimethyldisilane. Those skilled in the art will understand that somewhat different fractions may be selected by different manufacturers, but the term "disilane fraction" as used herein is broad enough to cover such fractions.

ILLUSTRATIVE EXAMPLES OF THE INVENTION

In this application there is shown and described preferred embodiments of the invention and suggested various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it, each as may be best suited in the condition of a particular case.

EXAMPLE 1

200 g of disilane fraction is mixed with 500 cm$^3$ of 2 M solution of methyl magnesium chloride in tetrahydrofuran with stirring at room temperature. After hydrolysis, the product hexamethyldisilane is washed with water to remove the tetrahydrofuran and magnesium chloride, and dried over molecular sieve pellets. A quantity of 100 grams (75% yield) of hexamethyldisilane is obtained. A quantity of 200 grams of disilane fraction and 3 grams AlCl$_3$ are then added to this hexamethyldisilane. The mixture is heated to reflux. The temperature of the refluxing vapors is initially about 113° C., and rises gradually over a period of about 1½ hours to 148° C. The product is then allowed to cool slowly down to room temperature. The product is analyzed to be about 75–80% pure 1,2 dichlorotetramethyldisilane. Most of the "impurity" is pentamethylchlorodisilane.

EXAMPLE 2

Example 1 was repeated, with the change that NaAlCl$_4$ catalyst was used instead of the AlCl$_3$. The catalyst was held on pellets of an aluminosilicate having high surface area. The catalyst pellets were weighed, soaked in a concentrated sodium chloride solution for several hours, drained, dried at 200° C. and reweighed. A stoichiometric amount of aluminum chloride (corresponding to the NaCl weight gain of the pellets) was mixed with the pellets and heated to about 300° C. Approximately 7 gm of NaAlCl$_4$ was distributed in this way on 100 gm of pellets, to serve as the catalyst. The results are very similar to Example 1.

EXAMPLE 3

Example 1 was repeated, with the addition of 10 g of 1,1,2,2 tetramethyldisilane (Me$_4$Si$_2$H$_2$). The reaction was substantially complete within about one-half (½) hour.

While the foregoing example demonstrates an illustrative use of high grade aluminum chloride products (mostly commercial) it is preferred to use larger quantities of aluminum chlorides because of the lower activity of some products. Quantities of 3 to 5% (e.g. 9 to 5 grams in Ex. 1) are more reliable. Still more reliable, in the sense of reproducing results, are procedures whereby the catalyst is formed in situ.

Aluminum chloride can be formed by in situ reaction. This this method is preferable from the point of view of the chemist, although it may complicate the handling of chemicals in a manufacturing plant. Among methods of in situ formation are reaction of trimethylaluminum or other alkylaluminum component with the methylchlorodisilane mixture. Also, aluminum chloride may be supplied by the selfpurifying sublimation of the compound whereby the sublimed material is transported to the reaction mix.

It is also to be understood that the following claims are intended to cover all of the generic and specific features of the invention herein described and all statements of the scope of the invention which might be said to fall therebetween.

What is claimed is:

1. A process for synthesizing chloromethyldisilanes starting from the disilane fraction resulting from the direct process for the manufacture of silicones, said process comprising the steps of
    (a) reacting said disilane fraction with a methylating agent to form hexamethyldisilane and
    (b) reacting said hexamethyldisilane with a further portion of said disilane fraction to form a chloromethyldisilane product.

2. A process as defined in claim 1 wherein said reaction (b) is carried out in the presence of a catalyst.

3. A process as defined in claim 1 wherein said reaction (b) is carried out at elevated temperatures.

4. A process as defined in claim 2 wherein said reaction (b) is carried out at elevated temperatures.

5. A process as in claim 2, in which said catalyst contains one or more of the following: aluminum chloride AlCl$_3$, sodium chloroaluminate NaAlCl$_4$, boron trichloride BCl$_3$, gallium trichloride GaCl$_3$, zirconium chloride ZrCl$_4$ and tin chloride SnCl$_4$.

6. A process as defined in claim 2 wherein said reaction between hexamethyldisilane and said disilane fraction is carried out in the presence of a co-catalyst of the formula Me$_{6-x}$Si$_2$H$_x$ where x is any of the integers 1 through 4.

7. A process as defined in claim 4 wherein said reaction between hexamethyldisilane and said disilane fraction is carried out in the presence of a co-catalyst of the formula Me$_{6-x}$Si$_2$H$_x$ where x is any of the integers 1 through 4.

8. A process as in claims 1, 2, 3, 4, 5, 6 or 7 in which stoichiometric proportions of the reactants are so selected that the product is mainly 1,2-dichloro 1,1,2,2-tetramethyldisilane.

9. A process as in claims 1, 2, 3, 4, 5, 6 or 7 in which stoichiometric proportions of the reactants are so selected that the product is mainly 1,1,2 trichloro 1,2,2-trimethyldisilane.

10. A process as in claim 1, 2, 3, 4, 5, 6 or 7 in which stoichiometric proportions of the reactants are so selected that the product is mainly chloropentamethyldisilane.

11. A process as defined in any of claims 1, 2, 3, 4, 5, 6 or 7 wherein said process comprises the additional step of (1) analyzing the chloromethyldisilane product after said step (b) and (2) reacting said product with sufficient additional of either a disilane fraction or with hexamethyldisilane to achieve an improved yield of a product selected from the group consisting of 1,2 dichloro 1,1,2,2-tetramethyldisilane; 1,1,2 trichloro 1,2,2-trimethyldisilane; an chloropentamethyldisilane.

12. A process as defined in claims 1, 2, 3, 4, 5, 6 or 7 wherein the yield of product is over 75–80% by weight of the reaction products.

13. A process as defined in claims 1, 2, 3, 4, 5, 6, or 7 wherein the yield of product is over 90% by weight of the reaction products.

14. A process for making a haloalkyldisilane product from a mixture of disilanes, which mixture comprises a mixture of trialkyl- and dialkylhalogenated disilanes, said process comprising the steps of
    (a) reacting said mixture with an alkylating agent to form a hexa-alkyldisilane and
    (b) reacting said hexa-alkyldisilane with a further portion of said mixture stoichiometrically selected to form said haloalkyldisilane product.

15. A process as defined in any of claims 1, 2, 4, 5, 6 or 7 wherein said disilane fraction has a boiling point from about 148° C. to 160° C. and has, at its primary constituents, Me$_2$Si$_2$Cl$_4$ and Me$_3$Si$_2$Cl$_3$.

16. A process as defined in claims 1, 2, 3, 4, 5, 6 or 7 wherein the yield of product is over 75%.

17. A process as defined in claim 8 wherein the yield of product is over 90% by weight of the reaction products.

18. A process as defined in claim 9 wherein the yield of product is over 90% by weight of the reaction products.

19. A process as defined in claim 10 wherein the yield of product is over 90% by weight of the reaction products.

20. A process as defined in claim 11 wherein the yield of product is over 90% by weight of the reaction products.

21. A process as defined in claim 11 wherein said disilane fraction has a boiling point from about 148° C. to 160° C. and has, as its primary constituents, $Me_2Si_2Cl_4$ and $Me_3Si_2Cl_3$.

22. A process as defined in claim 11 wherein the yield of product is over 75%.

* * * * *

UNITED STATES PATENT AND TRADEMARK OFFICE
CERTIFICATE OF CORRECTION

PATENT NO. : 4,289,890

DATED : September 15, 1981

INVENTOR(S) : Roy G. Gordon

It is certified that error appears in the above-identified patent and that said Letters Patent are hereby corrected as shown below:

Column 5, line 35 - Change "results are very similar" to --results were very similar--;

Column 5, line 52 - Change "This this method is preferable" to --This method is preferable--;

Column 6, line 49 - Change "trimethyldisilane; an" to --trimethyldisilane; and--;

Column 6, line 67 - Change "and has, at its primary" to --and has, as its primary--.

Signed and Sealed this

Twenty-sixth Day of January 1982

[SEAL]

Attest:

GERALD J. MOSSINGHOFF

*Attesting Officer*    *Commissioner of Patents and Trademarks*